US009498343B2

(12) United States Patent
Nevins

(10) Patent No.: US 9,498,343 B2
(45) Date of Patent: Nov. 22, 2016

(54) IMPLANT SYSTEM FOR KNEE PROSTHESIS

(71) Applicant: Russell Nevins, Las Vegas, NV (US)

(72) Inventor: Russell Nevins, Las Vegas, NV (US)

( * ) Notice: Subject to any disclaimer, the term of this patent is extended or adjusted under 35 U.S.C. 154(b) by 0 days.

(21) Appl. No.: 14/713,913

(22) Filed: May 15, 2015

(65) Prior Publication Data

US 2016/0022426 A1 Jan. 28, 2016

(30) Foreign Application Priority Data

Jul. 25, 2014 (AU) ................................ 2014902890

(51) Int. Cl.
*A61F 2/38* (2006.01)
*A61F 2/30* (2006.01)

(52) U.S. Cl.
CPC ............. *A61F 2/389* (2013.01); *A61F 2/3886* (2013.01); *A61F 2002/30014* (2013.01); *A61F 2002/30365* (2013.01); *A61F 2002/30433* (2013.01); *A61F 2002/30434* (2013.01); *A61F 2002/30593* (2013.01); *A61F 2002/30616* (2013.01); *A61F 2002/30772* (2013.01); *A61F 2002/30897* (2013.01); *A61F 2002/30901* (2013.01); *A61F 2310/00029* (2013.01)

(58) Field of Classification Search
CPC .............................. A61F 2/389; A61F 2/3868
See application file for complete search history.

(56) References Cited

U.S. PATENT DOCUMENTS

| | | | | | |
|---|---|---|---|---|---|
| 5,007,933 | A * | 4/1991 | Sidebotham | A61F 2/3886 | 623/20.27 |
| 5,609,641 | A * | 3/1997 | Johnson | A61F 2/389 | 623/20.32 |
| 2004/0049286 | A1* | 3/2004 | German | A61F 2/30734 | 623/20.33 |
| 2008/0188943 | A1* | 8/2008 | Gundlapalli | A61F 2/30942 | 623/20.28 |
| 2013/0304220 | A1* | 11/2013 | Bonitati | A61F 2/30734 | 623/20.15 |

* cited by examiner

*Primary Examiner* — Jason-Dennis Stewart
(74) *Attorney, Agent, or Firm* — Weide & Miller, Ltd.

(57) ABSTRACT

An implant system for knee prosthesis includes a superiorly located femoral bearing block having a femoral component bearing surface and an inferiorly located stem selectively attachable to the bearing block. A strengthening rod is disposed within at least a portion of the femoral bearing block and the stem.

20 Claims, 4 Drawing Sheets

SECTION A-A

IMPLANT SYSTEM FOR KNEE PROSTHESIS

CROSS REFERENCE TO RELATED APPLICATION

This application claims priority to Australian Application No. 2014902890 which was filed on Jul. 25, 2014, the contents of which are incorporated by reference.

BACKGROUND

1. Field of the Disclosure

The disclosure relates generally to orthopedic implants, and more particularly, but not necessarily entirely, to an implant system for knee prosthesis and more particularly a cemented system for tibial implant.

The disclosure has been developed primarily for use in tibial implants and will be described hereinafter with reference to this application. However, it will be appreciated that the disclosure is not limited to this particular field of use.

2. Background of the Disclosure

In total knee arthroplasty, the knee joint is replaced with an artificial knee implant.

The knee implant traditionally includes a femoral component and a tibial component. It is common practice to ream a portion of the bone (the distal end of the femur and the proximal portion of the tibia) to provide a channel to receive a stem of the respective the femoral component and the tibial component. A first knee replacement is referred to as a primary surgery. Fixation of the implant to the bone (femur or tibia) in a primary surgery may be achieved through cementing the implant to the bone or biologic fixation (non-cemented techniques) or otherwise.

In some cases, over time, implants may fail for one reason or another. For example, wear, infection, improper loading of the bone followed by loosening of the implant in the bone are reasons for implant failure. In such cases, a revision surgery may be required to properly fix the implant to the bone.

Despite the advantages of modern knee replacement systems, improvements are still being sought. The disclosure relates to an implant system for knee prosthesis for cemented tibial implant that may be used in primary or revision surgery.

The disclosure minimizes, and in some aspects eliminates, the failures encountered in modern tibial components by utilizing the methods and structural features described herein.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out herein.

It is to be understood that, if any prior art information is referred to herein, such reference does not constitute an admission that the information forms part of the common general knowledge in the art.

SUMMARY OF THE DISCLOSURE

According to a first exemplary embodiment, there is provided an implant system for knee prosthesis, the system comprising a superiorly located femoral bearing block having a femoral component bearing surface; an inferiorly located stem selectively attachable to the bearing block; and a strengthening rod within at least a portion of the femoral bearing block and the stem.

At least one of the stem and the bearing block may define a superior-inferior orientated shaft adapted for the removable receipt of the strengthening rod therein.

The shaft may extend through a superior surface of the bearing block so as to allow for the superior access to the strengthening rod.

The width of the shaft may be selected for the substantial frictional engagement of the strengthening rod for substantially reducing the movement of the strengthening rod in relation to the shaft in use.

The strengthening rod may comprise a friction enhancing surface.

The femoral bearing block and the stem may be shaped to form a mechanical interlock.

The mechanical interlock may be adapted to substantially inhibit the rotation of the stem with respect to the bearing block in use.

The femoral bearing block may define an inferiorly located terraced geometry adapted for engaging a proximal end of the tibia in use.

The terraced geometry may comprise a plurality of terraces, each of the plurality of terraces defining a lateral surface substantially perpendicular to an axis of insertion of the stem adapted to substantially reduce hoop stress exerted by the terraced geometry on the proximal end of the tibia by the in use.

The terraced geometry may comprise a non-rotational cross section.

The implant system may further comprise a further stem wherein the stem and the further stem comprise at least one differing geometry.

The at least one differing geometry may comprise at least one of width and length.

At least one of the femoral bearing block and the stem may be manufactured from a polymer.

The polymer may comprise polyethylene.

The strengthening rod may be manufactured from metal.

The strengthening rod may be a chrome plated cobalt rod.

Other aspects are also disclosed.

BRIEF DESCRIPTION OF THE DRAWINGS

Notwithstanding any other forms which may fall within the scope of the present disclosure, preferred embodiments of the disclosure will now be described, by way of example only, with reference to the accompanying drawings in which.

DESCRIPTION OF EMBODIMENTS

Figure 1:
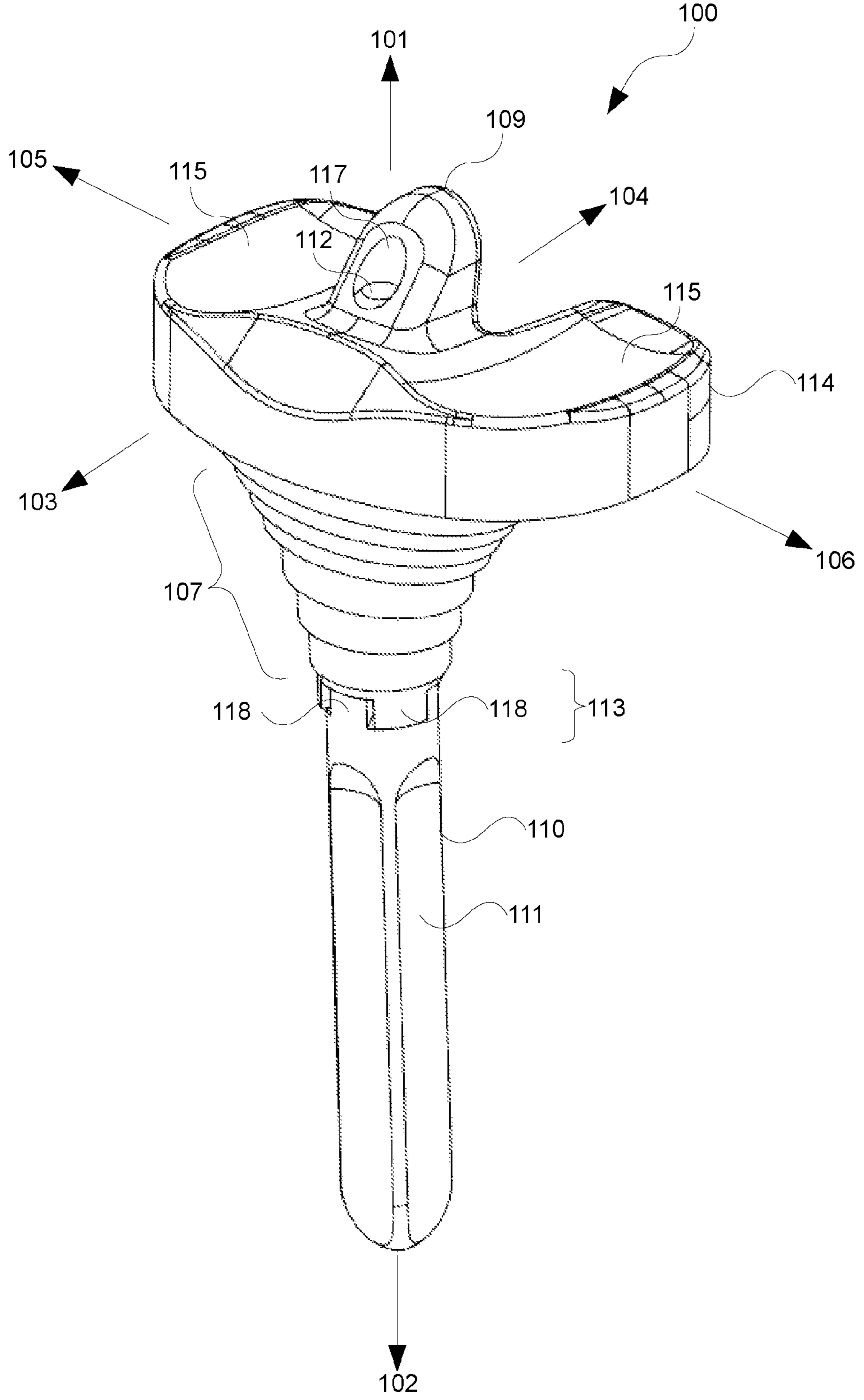
FIG. 1 shows an implant system for a knee prosthesis in accordance with a preferred embodiment of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure.

Before the structures, systems and associated methods relating to the implant system for knee prosthesis are disclosed and described, it is to be understood that this disclosure is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the disclosure will be limited only by the claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterised by," and grammatical equivalents thereof are inclusive or open-ended terms that do not exclude additional, unrecited elements or method steps.

It should be noted in the following description that like or the same reference numerals in different embodiments denote the same or similar features.

Turning now to FIG. 1, there is shown an implant system 100 for knee prosthesis. Specifically, the implant system 100 is adapted for use as a tibial component for artificial knees, including for primary and revision surgery. The implant system 100 is adapted for insertion into the proximal end of a resected tibia to provide a bearing surface for a complimentary femoral component (not shown) inserted into a distal end of a resected femur.

For orientation purposes, there is shown the anterior side 103, posterior side 104, median side 105, lateral side 106, superior side 101 and inferior side 102. Furthermore, reference to the proximal end of the tibia refers to the end of the tibia at the knee joint and the distal end of the tibia refers to the end of the tibia towards the foot.

The implant system 100 comprises a superiorly located bearing block 114 adapted to provide a femoral component bearing surface. In this manner, the bearing block 114 comprises a plurality of condylar regions 115 adapted for bearing against complimentary shaped femoral component condyles (not shown) in use. In an embodiment, the bearing block 140 may comprise a femoral component engagement ridge 109 including to provide lateral stability at the interface between the bearing block 114 and the femoral component.

The implant system 100 further comprises a stem 110 adapted for insertion into a proximal end of a resected tibia. In the embodiments described herein, the stem 110 is preferably adapted for cemented implantation and may therefore, as will be described in further detail below, be manufactured from a less resilient material compared to metal implant components, such as the stem 110 being manufactured from a polymer, such as polyethylene. However, it should be noted that in alternative embodiments, the stem 110 may be adapted for cementless implant also.

As is apparent, the stem 110 is inferiorly located beneath the bearing block 114.

In preferred embodiments, the stem 110 is selectively attachable to the bearing block 114 to allow for the selection of an appropriate stem 110 by an orthopaedic surgeon for use in an operation. For example, differing conditions may warrant differing stem 110 geometry, such as whether the operation is a primary or revision surgery, the geometry and condition of the tibia and the like. In this manner, in this preferred embodiment, the implant system 100 is provided with a plurality of stems 110 each having differing geometries, such as differences in width, length and the like. During an operation, the surgeon is able to select the most appropriate stem 110 for attachment to the bearing block 114.

The implant system 100 further comprises a strengthening rod 112 adapted for strengthening the implant system 100. Specifically, referring to FIG. 3B, there is shown a cross-sectional view of the implant system 100 wherein the strengthening rod 112 is shown within the femoral bearing block 114 and the stem 110.

The strengthening rod 110 provides strength and rigidity to the implant system 100, especially where the bearing block 114 and the stem 110 are manufactured from less resilient but more cost effective polymers, such as polyethylene. In this manner, the system 110 may be manufactured from lower cost material.

In one embodiment, the strengthening rod 110 comprises metal such as cobalt. Furthermore, the cobalt may be plated such as by being chrome plated.

Figure 2:
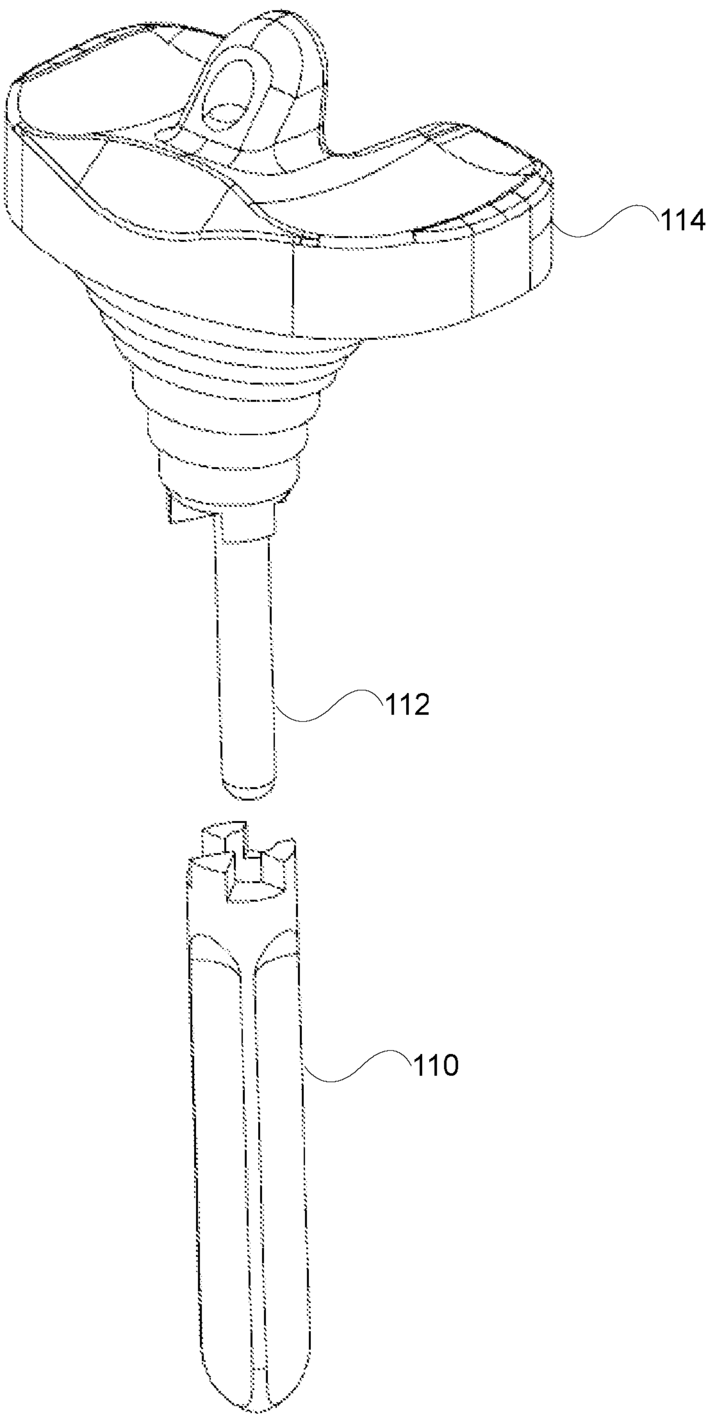
FIG. 2 shows the implant system of FIG. 1 in a disassembled configuration in accordance with a preferred embodiment of the present disclosure.

In a preferred embodiment, the shaft 116 of the stem 110 is adapted for the removable receipt of the strengthening rod 112 therein. Specifically, referring to FIG. 2, there is shown the implant system 100 in a disassembled configuration wherein the strengthening rod 112 is shown as having been removed from the stem 110.

As is apparent from the embodiment presented in FIG. 3, the stem 110 and the bearing block 140 each define a superior-inferior orientated shaft 116 adapted for containing the strengthening rod 112 therein.

In this embodiment, the shaft 116 of the bearing block 114 may extend through the superior surface of the bearing block 114 so as to provide an access opening 117 for the access of the strengthening rod 112 in use. In this embodiment, in use, the stem 110 may be inserted into the proximal end of the tibia and the bearing block 114 subsequently located to adjacent the implanted stem 110. Thereafter, the orthopaedic surgeon is able to drive the strengthening rod 112 through the access opening 117 through the bearing block 114 and into the stem 110. The surgeon may drive the rod 112 beyond the access opening 117 utilising an appropriately elongate hammer utensil or the like.

The preferred embodiment, the width of the shaft 116 is sized in accordance with the width of the strengthening rod 112 to provide for these substantial frictional engagement of the rod 112 by the shaft 116 to substantially reduce the movement of the strengthening rod 112 with respect to the shaft 116. In embodiments, the strengthening rod 112 may comprise a rough frictional enhancing surface or the like to enhance the frictional engagement of the rod 112 by the shaft 116.

It should be noted that in other embodiments, the strengthening rod 112 may be fixed within the bearing block 114 for insertion into the stem 110 in use. In another embodiment, the strengthening rod 112 may be fixed within the stem 110 for insertion into the bearing block 114.

Referring again to FIG. 1, the bearing block 114 and the stem 110 are adapted to form a mechanical interlock 113. In this manner, each of the bearing block 114 and the stem 110 shaped to define complimentary mechanical interlock portions adapted to cooperate to form the mechanical interlock 113. In a preferred embodiment, the mechanical interlock 113 is adapted to restrict the substantial rotation of the bearing block 114 with respect to the stem 110. In this manner, in one embodiment, the mechanical interlock portions comprise complimentary battlements 118, each battlement 118 comprising a substantially vertical portion adapted to abut against an adjacent battlement 118 to restrict the rotation of the bearing block 114 with respect to the stem 110.

In one embodiment, the battlements 118 of the stem 110 have a width slightly narrower than that of the battlements of the bearing block 114. As such, the mechanical interlock 113 allows for the slight rotation of the bearing block 114 with respect to the stem 110 so as to, for example, allow the surgeon to select the most appropriate rotation of the bearing block 114 with respect to the stem 110 in use prior to driving the strengthening rod 112 through the shaft 116.

It should be noted that in other embodiments other mechanical interlock's 113 may be employed also.

Referring again to FIG. 1, there is shown the inferior side of the bearing block 114 comprising terraced geometry 107 comprising a plurality of terraces 108.

The terraced geometry 107 is adapted for engaging the proximal end of the tibia in use in a manner that reduces hoop stress exerted by the terraced geometry 107 on the tibia. Specifically, hoop stress would unduly stress the tibia resulting in stress fractures, loosening of the implant system 100 and the like.

Figure 3A:
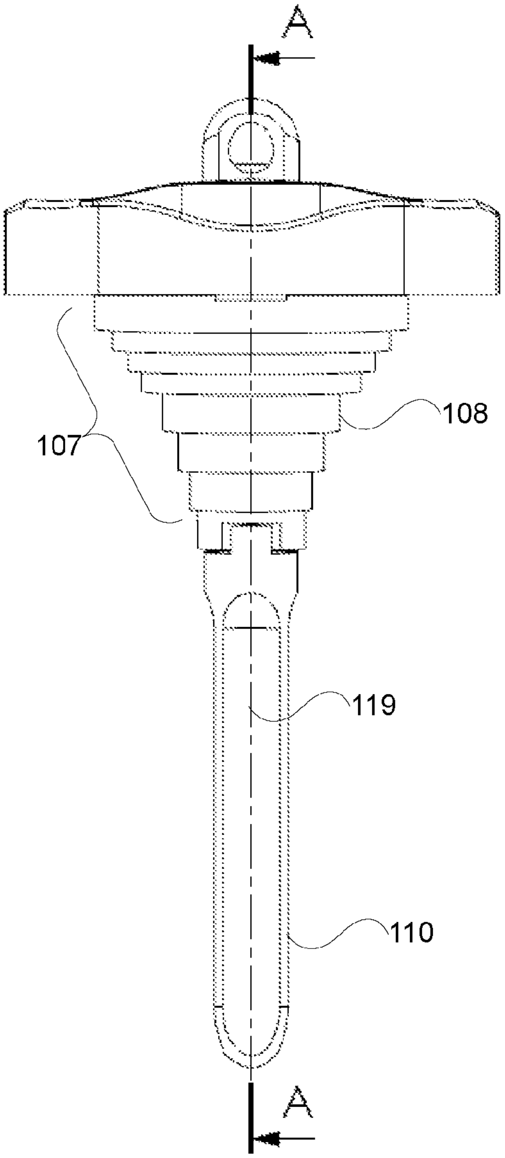
FIGS. 3A and 3B show a front elevation and side cross-sectional view of the implant system of FIG. 1 in accordance with a preferred embodiment of the present disclosure.
Figure 3B:
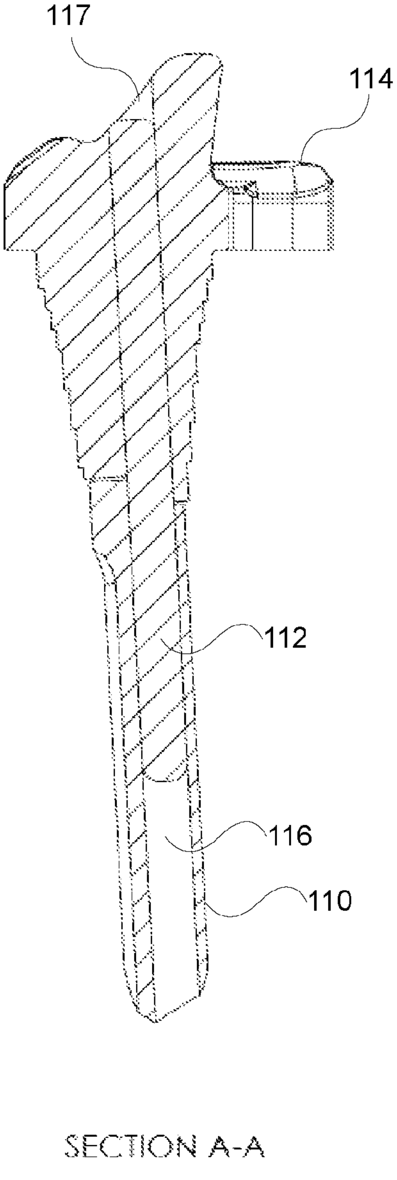

As is apparent from the embodiment provided in FIG. 3A, the lateral surfaces of each terrace 108 is substantially perpendicular to the axis of insertion 119 for eliminating or reducing lateral forces on the tibia. In other words, the terraced geometry 107 as substantially devoid of surfaces having an acute angle with respect to the axis of insertion 119 which would exert lateral forces of the proximal end of the tibia when the terraced geometry 107 is loaded.

During insertion, the proximal end of the tibia may be reamed to form a cavity to complement the profile of the terraced geometry 107. Alternatively, and as alluded to above in a preferred embodiment where the bearing block 114 comprises a polymer, the terraced geometry 107 may be shaped using appropriate cutting and rasping tools in use to achieve a desired geometry for accommodation by the proximal end of the tibia.

In the preferred embodiment shown in the accompanying drawings, the bearing block 114 comprises the terraced geometry 107. However, in other embodiments, the stem 110 may define the terraced geometry 107. In these other embodiments, the terraced geometry 107 of the stem 110 is adapted for engaging the bearing block 114 using a suitable mechanical attachment.

In a yet further embodiment, the implant system 100 may comprise three components comprising: the bearing block 114; a separate terraced geometry component (not shown), and the stem 110, wherein the bearing block 114 is adapted for attachment to the separate terraced geometry component 107 and the separate terraced geometry component is adapted for attachment to the stem 110. In this embodiment, differing stems 110, terraced geometry components and bearing blocks 114 may be selected by a surgeon for implanting.

Figure 4A:
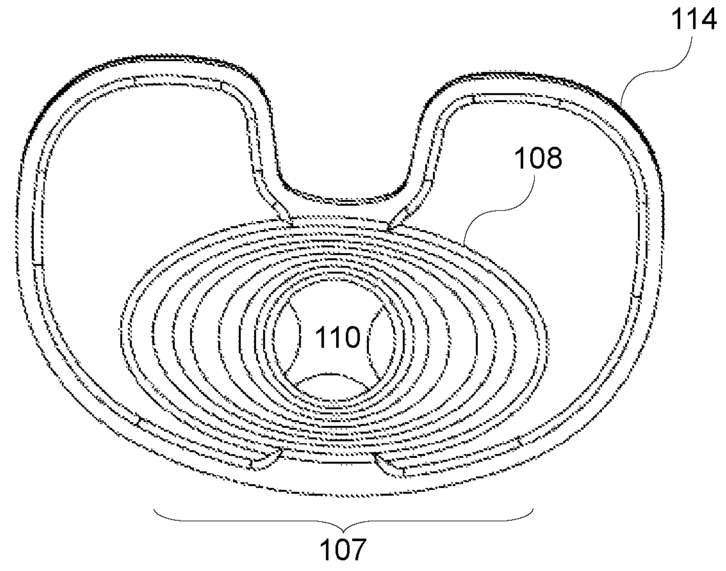
FIGS. 4A and 4B show top and bottom views the implant system of FIG. 1 in accordance with a preferred embodiment of the present disclosure.
Figure 4B:
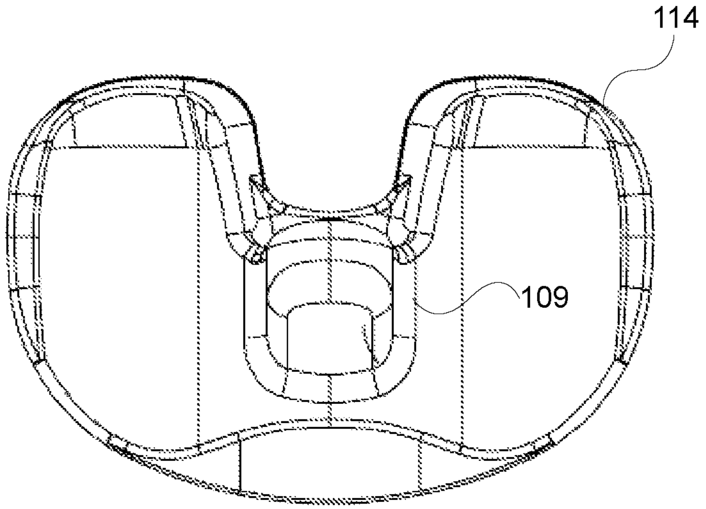

Referring now to FIG. 4A there is shown the inferior view of the implant system 100 and especially the terraced geometry 107 in further detail. In a preferred embodiment, the terraced geometry 107 comprises a non-rotational cross-section so as to substantially prevent the rotation of the bearing block 114 with respect to the tibia. In the embodiment provided, the terraced geometry 107 comprises an ellipse-shaped cross section, the ellipse cross section substantially preventing the rotation of the terraced geometry 107 within the proximal portion of the tibia.

It should be noted that another embodiment, the terraced geometry 107 may comprise other cross-section is adapted for preventing the rotation of the terraced geometry 107 with respect to the tibia. Such cross sections may comprise other non-rotational cross-sections, such as squares, triangles, rectangles and the like. Furthermore, the terrace to geometry 107 cross-section may comprise outward protrusions to enhance the engagement of the tibia by the stepped geometry portion 107.

INTERPRETATION EMBODIMENTS

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Specific Details

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Terminology

In describing the preferred embodiment of the disclosure illustrated in the drawings, specific terminology will be resorted to for the sake of clarity. However, the disclosure is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Comprising and Including

In the claims which follow and in the preceding description of the disclosure, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the disclosure.

Any one of the terms: including or which includes or that includes as used herein is also an open term that also means including at least the elements/features that follow the term, but not excluding others. Thus, including is synonymous with and means comprising.

Scope of Disclosure

Thus, while there has been described what are believed to be the preferred embodiments of the disclosure, those skilled in the art will recognize that other and further modifications may be made thereto without departing from the spirit of the disclosure, and it is intended to claim all such changes and modifications as fall within the scope of the disclosure. For example, any formulas given above are merely representative of procedures that may be used. Functionality may be added or deleted from the block diagrams and operations may be interchanged among functional blocks. Steps may be added or deleted to methods described within the scope of the present disclosure.

Although the disclosure has been described with reference to specific examples, it will be appreciated by those skilled in the art that the disclosure may be embodied in many other forms.

The invention claimed is:

1. An implant system for knee prosthesis, the system comprising:

a superiorly located femoral bearing block having a femoral component bearing surface;

an inferiorly located stem selectively attachable to the bearing block, the stem configured to be cemented into a resected tibia; and a strengthening rod within at least a portion of the femoral bearing block and the stem wherein the femoral bearing block and the stem are formed from a polymer.

2. An implant system as claimed in claim 1, wherein at least one of the stem and the bearing block defines a superior-inferior orientated shaft adapted for the removable receipt of the strengthening rod therein.

3. An implant system as claimed in claim 2, wherein the shaft extends through a superior surface of the bearing block so as to allow for the superior access to the strengthening rod.

4. An implant system as claimed in claim 2, wherein the width of the shaft is selected for the substantial frictional engagement of the strengthening rod for substantially reducing the movement of the strengthening rod in relation to the shaft in use.

5. An implant system as claimed in claim 4, wherein the strengthening rod comprises a friction enhancing surface.

6. An implant system as claimed in claim 1, wherein the femoral bearing block and the stem are shaped to form a mechanical interlock.

7. An implant system as claimed in claim 6, wherein the mechanical interlock is adapted to substantially inhibit the rotation of the stem with respect to the bearing block in use.

8. An implant system as claimed in claim 1, wherein the femoral bearing block defines an inferiorly located terraced geometry adapted for engaging a proximal end of the tibia in use.

9. An implant system as claimed in claim 8, wherein the terraced geometry comprises a plurality of terraces, each of the plurality of terraces defining a lateral surface substantially perpendicular to an axis of insertion of the stem adapted to substantially reduce hoop stress exerted by the terraced geometry on the proximal end of the tibia in use.

10. An implant system as claimed in claim 8, wherein the terraced geometry comprises a non-rotational cross section.

11. An implant system as claimed in claim 1, further comprising a further stem wherein the stem and the further stem comprise at least one differing geometry.

12. An implant system as claimed in claim 11, wherein the at least one differing geometry comprises at least one of width and length.

13. An implant system as claimed in claim 1, wherein the polymer comprises polyethylene.

14. An implant system as claimed in claim 1, wherein the strengthening rod is manufactured from metal.

15. An implant system as claimed in claim 14, wherein the strengthening rod is a chrome plated cobalt rod.

16. An implant for knee prosthesis, the implant comprising:

a superiorly located femoral bearing block having a femoral component bearing surface;

an inferiorly located stem selectively attachable to the bearing block;

a terraced geometry portion disposed between the femoral bearing block and the stem, the femoral bearing block, the stem, and the terraced geometry portion all being constructed from a polymer; and a strengthening rod disposed within at least a portion of the femoral bearing block, the terraced geometry portion, and the stem, the strengthening rod being constructed from a metal.

17. The implant of claim 16, wherein the stem is configured to be cemented within a proximal end of a resected tibia, and the terraced geometry portion is configured to engage with the proximal end of the tibia to prevent rotation of the implant with respect to the tibia.

18. The implant of claim 17, wherein the terraced geometry portion comprises an ellipse-shaped cross-section.

19. The implant of claim 16, wherein the terraced geometry portion is configured to be cuttable to correspond to a profile of a proximal end of a tibia.

20. The implant of claim 16, wherein the femoral bearing block, the stem, and the terraced geometry portion are separately constructed, the femoral bearing block and the terraced geometry portion are adapted for attachment to one another, and the terraced geometry portion and the stem are adapted for attachment to one another.

* * * * *